(12) United States Patent
Dyer et al.

(10) Patent No.: US 12,115,353 B2
(45) Date of Patent: Oct. 15, 2024

(54) ROTARY MOTOR BASED TRANSDERMAL INJECTION DEVICE

(71) Applicant: Portal Instruments, Inc., Cambridge, MA (US)

(72) Inventors: Robert J. Dyer, Cambridge, MA (US); Carl Tappan, Cambridge, MA (US); Eric VanWyk, Cambridge, MA (US)

(73) Assignee: Portal Instruments, Inc., Cambridge, MA (US)

( * ) Notice: Subject to any disclaimer, the term of this patent is extended or adjusted under 35 U.S.C. 154(b) by 996 days.

(21) Appl. No.: 17/102,958

(22) Filed: Nov. 24, 2020

(65) Prior Publication Data

US 2021/0077730 A1    Mar. 18, 2021

Related U.S. Application Data

(63) Continuation of application No. 16/573,391, filed on Sep. 17, 2019, now Pat. No. 10,850,038, which is a
(Continued)

(51) Int. Cl.
*A61M 5/30* (2006.01)
*A61M 5/145* (2006.01)
(Continued)

(52) U.S. Cl.
CPC ........ *A61M 5/3007* (2013.01); *A61M 5/1452* (2013.01); *A61M 5/16877* (2013.01);
(Continued)

(58) Field of Classification Search
CPC ............. A61M 5/3007; A61M 5/1452; A61M 5/16877; A61M 5/48; A61M 5/172;
(Continued)

(56) References Cited

U.S. PATENT DOCUMENTS

| 3,424,154 A | 1/1969 | Kinsley |
| 5,505,697 A | 4/1996 | McKinnon, Jr. et al. |

(Continued)

FOREIGN PATENT DOCUMENTS

| CN | 1571684 A | 1/2005 |
| CN | 105979992 A | 9/2016 |

(Continued)

OTHER PUBLICATIONS

International Search Report and Written Opinion, PCT Application No. PCT/US2018/050643, mailed Dec. 7, 2018 (15 pages).
(Continued)

*Primary Examiner* — Laura A Bouchelle
*Assistant Examiner* — Sarah Dympna Grasmeder
(74) *Attorney, Agent, or Firm* — Strategic Patents, P.C.

(57) ABSTRACT

An apparatus for injectate delivery includes a cartridge, a linear actuator, a rotary motor mechanically coupled the actuator, and a controller coupled to the motor. The controller controls a linear motion of the actuator by controlling an electrical input supplied to the motor in a first interval during which the motor is stationary with the linear actuator engaged with the cartridge to displace an injectate in the cartridge, a second interval following the first interval during which the controller accelerates the motor from stationary to a first speed selected to create a jet of the injectate from the cartridge with a velocity sufficient to pierce human tissue to a subcutaneous depth, a third interval during which the controller maintains the motor at or above the first speed, and a fourth interval during which the controller decelerates the motor to a second speed to deliver the injectate at the subcutaneous depth.

20 Claims, 7 Drawing Sheets

Related U.S. Application Data continuation of application No. 16/129,241, filed on Sep. 12, 2018, now Pat. No. 10,413,671.

(60) Provisional application No. 62/557,381, filed on Sep. 12, 2017.

(51) Int. Cl.
  *A61M 5/168* (2006.01)
  *A61M 5/172* (2006.01)
  *A61M 5/20* (2006.01)
  *A61M 5/48* (2006.01)

(52) U.S. Cl.
  CPC .............. *A61M 5/172* (2013.01); *A61M 5/20* (2013.01); *A61M 5/48* (2013.01); *A61M 2205/3327* (2013.01)

(58) Field of Classification Search
  CPC ...... A61M 5/30; A61M 5/482; A61M 5/3015; A61M 2205/3327; A61M 2205/103; A61M 2205/13; A61M 2005/3022
  See application file for complete search history.

(56) References Cited

U.S. PATENT DOCUMENTS

| | | | |
|---|---|---|---|
| 5,911,703 A | | 6/1999 | Slate et al. |
| 6,056,716 A | * | 5/2000 | D'Antonio ............ A61M 5/30 604/134 |
| 2001/0031945 A1 | | 10/2001 | Haar et al. |
| 2003/0173110 A1 | | 9/2003 | Gross et al. |
| 2007/0129693 A1 | | 6/2007 | Hunter et al. |
| 2008/0071218 A1 | * | 3/2008 | D'Antonio ............ A61M 5/30 604/152 |
| 2008/0091139 A1 | | 4/2008 | Srinivasan et al. |
| 2008/0214995 A1 | | 9/2008 | Boyd et al. |
| 2008/0278978 A1 | | 11/2008 | Czimmek |
| 2010/0016827 A1 | | 1/2010 | Hunter et al. |
| 2012/0095435 A1 | | 4/2012 | Hunter et al. |
| 2014/0378889 A1 | | 12/2014 | Tavger |
| 2015/0374387 A1 | | 12/2015 | Courtney, Jr. et al. |
| 2015/0374921 A1 | | 12/2015 | Kojic et al. |
| 2016/0271326 A1 | | 9/2016 | Slate et al. |
| 2016/0354559 A1 | | 12/2016 | Gavini et al. |
| 2017/0049966 A1 | | 2/2017 | Taberner et al. |
| 2017/0143906 A1 | * | 5/2017 | Coats ................ A61M 5/2033 |
| 2017/0224935 A1 | | 8/2017 | Hoffmann et al. |
| 2018/0304019 A1 | | 10/2018 | Oda et al. |

FOREIGN PATENT DOCUMENTS

| | | |
|---|---|---|
| CN | 107073216 A | 8/2017 |
| JP | 2001224684 A | 8/2001 |
| JP | 2013539688 A | 10/2013 |
| JP | 2014050743 A | 3/2014 |
| WO | 2017/115868 A1 | 7/2017 |
| WO | WO-2017115868 | 7/2017 |

OTHER PUBLICATIONS

IP India, "IN Application Serial No. 202027015765 Second Examination Report mailed Mar. 1, 2024", 3 pages.

USPTO, "U.S. Appl. No. 17/743,959 Non-Final Office Action mailed Aug. 27, 2024", 15 pages.

* cited by examiner

ROTARY MOTOR BASED TRANSDERMAL INJECTION DEVICE

CROSS REFERENCE TO RELATED APPLICATION

Under 35 USC 120, this application is a continuation of U.S. application Ser. No. 16/573,391, filed Sep. 17, 2019, now U.S. Pat. No. 10,850,038 issuing Dec. 1, 2020, which is a continuation of U.S. application Ser. No. 16/129,241, filed Sep. 12, 2018, now U.S. Pat. No. 10,413,671, which claims the benefit of the priority filing date of U.S. Provisional Application No. 62/557,381, filed Sep. 12, 2017, the contents of which are hereby incorporated by reference in their entirety.

BACKGROUND

This invention relates to a rotary motor based needle-free transdermal injection device.

Skin serves as a protective barrier to the body. In the field of modern medicine, drugs are often delivered through the skin into the bloodstream of patients. Traditionally, this is accomplished by insertion of a needle through the patient's skin and into a target area for an injection. However, the use of needles present significant drawbacks ranging from patient fear and discomfort to safety hazards associated with handling used needles.

Needle-free transdermal injection devices have been developed as an alternative to needle-based injectors. These devices typically use a high pressure, narrow jet of injectate to penetrate a patient's skin, obviating the need to pierce the patient's skin with a needle. However, there remains a need for improved needle-free injection devices.

SUMMARY

In a general aspect, an apparatus for injectate delivery includes a cartridge containing a volume of an injectate and an exit port, a linear actuator configured for delivery of the injectate from the exit port of the cartridge, the linear actuator including a linkage, a rotary motor mechanically coupled to the linkage, and a controller coupled to the rotary motor. The controller is configured to control a linear motion of the actuator in response to a control signal by controlling an electrical input supplied to the motor in a first interval during which the rotary motor is stationary and the linear actuator is engaged with the cartridge to displace the injectate therefrom, a second interval immediately following the first interval during which the controller accelerates the rotary motor from stationary to a first speed selected to create a jet of the injectate from the cartridge with a velocity at least sufficient to pierce human tissue to a subcutaneous depth, a third interval during which the controller maintains the rotary motor at or above the first speed, and a fourth interval during which the controller decelerates the rotary motor to a second speed selected to deliver the volume of the injectate at the subcutaneous depth.

Aspects may include one or more of the following features.

The controller may be configured to deliver a sequence of injections of the injectate from the volume without reverse movement of the rotary motor. The controller may be configured to deliver a sequence of injections of the injectate from the volume in close temporal proximity to one another. The volume may be at least one milliliter. The volume may be not greater than about 0.5 milliliters. The volume may be not greater than about 0.3 milliliters. The volume may be a therapeutic amount of the injectate. The injectate may be a biological drug.

The injectate may have a viscosity of at least three centipoise at a temperature between two degrees and twenty degrees Celsius. The injectate may have a viscosity of about three centipoise to about two hundred centipoise at a temperature between two degrees and twenty degrees Celsius. A second velocity of the jet of injectate from the cartridge during the second interval may reach at least two hundred meters per second. The rotary motor may provide sufficient power to reach the first speed in not more than three rotations.

A duration of the second interval may be less than hundred milliseconds. A duration of the second interval is less than sixty milliseconds. The second interval may be less than ten milliseconds. The linear actuator may be bidirectionally coupled to the rotary motor and the cartridge to permit bidirectional displacement of contents of the cartridge. The apparatus may include plurality of supercapacitors coupled to the rotary motor and configured to provide electrical power to the rotary motor during the second interval, the third interval and the fourth interval. The plurality of supercapacitors may be configured to charge in parallel and discharge to power the rotary motor in serial. The rotary motor and the plurality of supercapacitors may be configured to deliver a peak power to the linear actuator of at least two hundred Watts.

In another general aspect, an apparatus for injectate delivery includes a cartridge containing a volume of an injectate and an exit port, a linear actuator configured for delivery of the injectate from the exit port of the cartridge, the linear actuator including a linkage, a rotary motor mechanically coupled to the linkage, and a controller coupled to the rotary motor. The controller is configured to control a linear motion of the actuator in response to a control signal by controlling an electrical input supplied to the motor in a first interval during which the rotary motor is engaged with the cartridge to displace the injectate therefrom, a second interval immediately following the first interval during which the controller drives the rotary motor at a first speed selected to create a jet of the injectate from the cartridge with a velocity at least sufficient to pierce human tissue, a third interval during which the controller continues operating the motor at or above the first speed in order to maintain the jet of the injectate at or above the velocity and create a channel through the human tissue to a subcutaneous depth, and a fourth interval during which the controller decelerates the rotary motor to a second speed selected to deliver the volume of the injectate at the subcutaneous depth.

Aspects may include one or more of the following features.

The apparatus may include a sensor system configured to detect when the apparatus is properly positioned to deliver the injectate to a patient, wherein the controller and the rotary motor are configured to initiate delivery of the injectate without substantial observable latency when the apparatus is properly positioned. The sensor system may detect a contact of the apparatus with a skin of the patient. The sensor system may detect an angle of the cartridge relative to a skin of the patient. The sensory system may detect a position of the exit port relative to a body of the patient.

The capacitive energy storage element may include one or more supercapacitive energy storage elements. The one or more supercapacitive energy storage elements may include a plurality of supercapacitive energy storage elements and the supply circuitry is configured to switch the plurality of supercapacitive energy storage elements into a parallel configuration during a charging operation and to switch the plurality of supercapacitive energy storage elements into a serial configuration for an injection operation. The capacitive energy storage element may include a plurality of capacitors. The supply circuitry may be configured to switch the plurality of capacitors into a parallel configuration with the battery during a charging operation and to switch the plurality of capacitors into a serial configuration for an injection operation.

The supply circuitry may include a direct current to direct current (DC/DC) converter disposed between the battery and the capacitive energy storage element. The DC/DC converter may be configured to boost a voltage supplied by the battery by a factor in a range of 5-20. Substantially all of an electrical power supplied to the rotary motor during the second time interval and the third time interval may be supplied from the capacitive energy storage element. The injection controller may be configured to prevent multiple injectate delivery operations within a predetermined minimum injection cycle time. In some examples, the supply circuitry includes a DC/DC converter disposed between the capacitive energy storage element and the rotary motor.

The third time interval may be in a range of two to twenty times as long as the second time interval. The second time interval may have a first duration of between 30 milliseconds and 100 milliseconds and third time interval has a second duration of between 100 milliseconds and 1000 milliseconds.

The apparatus may include a cartridge removably and replaceably coupled to the apparatus, the cartridge containing an injectate and the cartridge including an exit port with a predetermined shape for ejecting the injectate in a stream. The electrical input supplied during the second time interval may be selected to drive the rotary motor at a speed sufficient to drive the stream from the exit port at a velocity to pierce human skin, and wherein a duration of the second time interval is selected to pierce the human skin with the stream to a subcutaneous depth. The electrical input supplied during the third time interval may be selected to deliver additional injectate from the cartridge at the subcutaneous depth.

Aspects may have one or more of the following advantages.

Use of an actively controlled rotary motor to drive a plunger into a cartridge allows for a rapid acceleration of the plunger into the cartridge. By rapidly accelerating the plunger into the cartridge, a piercing jet with high velocity is quickly attained. Use of supercapacitors in the power supply supports the rapid acceleration of the plunger since supercapacitors have capacitance values much higher than other capacitors and are able to store 10 to 100 times more energy per unit volume or mass than electrolytic capacitors. Supercapacitors can also accept and deliver charge much faster than batteries, and tolerate many more charge and discharge cycles than rechargeable batteries.

Other features and advantages of the invention are apparent from the following description, and from the claims.

DESCRIPTION

In the following document, references to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated, and each separate value within such a range is incorporated into the specification as if it were individually recited herein. The words "about," "approximately" or the like, when accompanying a numerical value or physical property, are to be construed as indicating a deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose or the like. Ranges of values and/or numeric values are provided herein as examples only, and do not constitute a limitation on the scope of the described embodiments unless explicitly stated otherwise. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms.

1 Needle-Free Transdermal Injection Device

Figure 1:
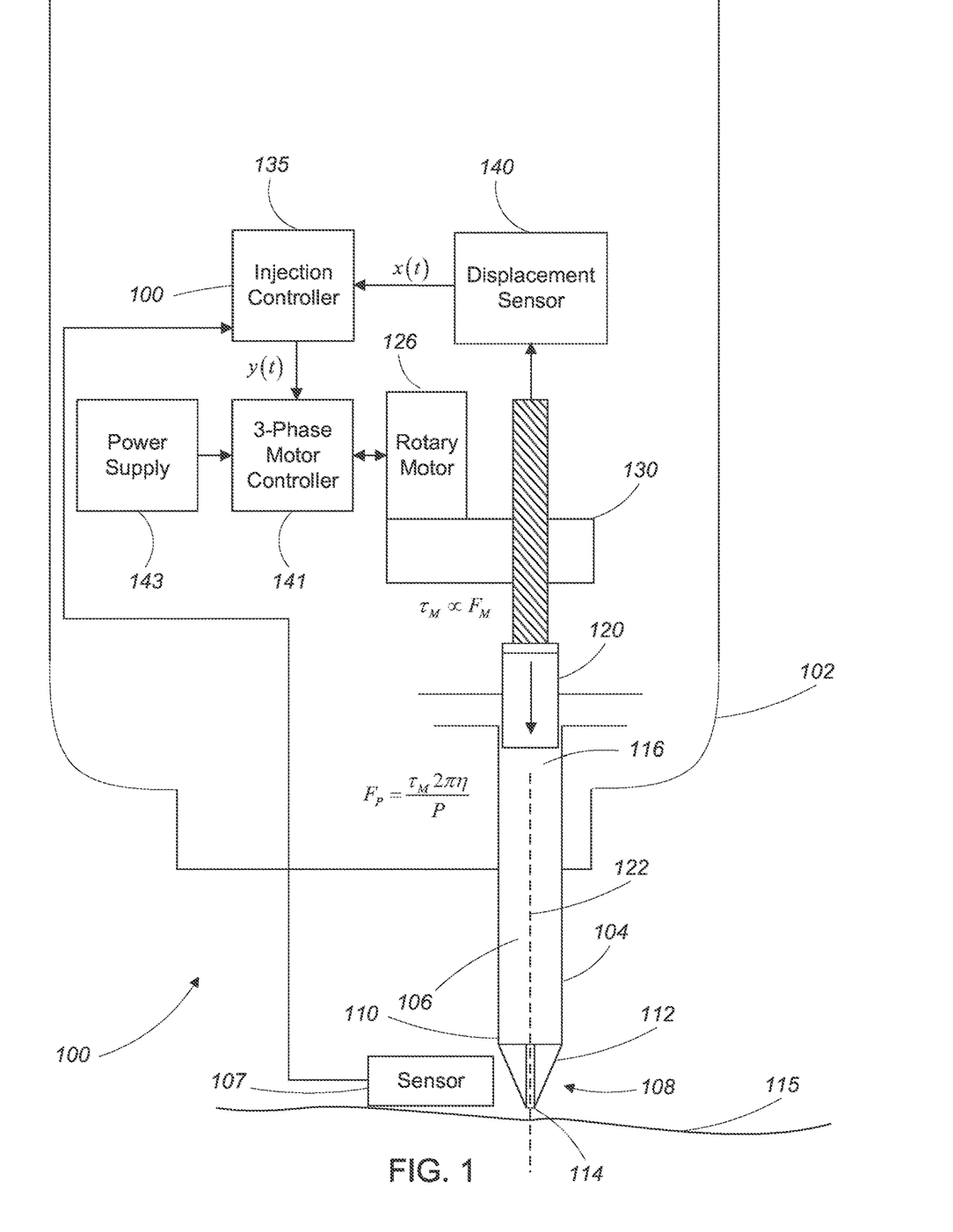
FIG. 1 is a schematic diagram of a controllable, needle-free transdermal injection device.

Referring to FIG. 1, a controllable, needle-free transdermal injection device 100 for transferring an injectate (e.g., a drug or a vaccine in any one of a number of states such as a liquid state or a powder state) through the skin of a patient includes a needle-free transdermal injector head 104 extending from a housing 102. The injector head 104 includes a chamber 106 for holding the injectate and a nozzle 108 disposed at a distal end 110 of the injector head 104. The nozzle 108 includes a head 112 and an opening 114 from which a jet of the injectate is discharged from the chamber 106. In operation, the opening 114 is placed near or against the skin 115 when the injectate is discharged.

The dimensions of the nozzle 108 may be adapted to control a shape and pressure profile of a stream of injectate exiting the nozzle 108. For example, the inner diameter of the opening 114 may be in a range of 50 μm to 300 μm, and may employ a taper along the longitudinal axis 122 toward the opening to shape an exiting stream of injectate. It will also be appreciated that the geometry of the chamber 106 relative to the opening 114 may affect how linear motion of a plunger or the like within the chamber 106 translates into an exit velocity or pressure by an injectate through the opening 114. An outer diameter of the head 112 of the nozzle 108 may narrow to the opening 114, or may remain uniform or may expand to provide a suitable resting surface for the head 112 of the nozzle 108. The nozzle 108 may have a length along the longitudinal axis 122 of about 500 μm to about 5 mm. Similarly, the chamber 106 may have any suitable length along the longitudinal axis for containing an injectate, and for displacing the injectate through the opening 114 in one or more needle-free injections.

The chamber 106 may have a proximal end 116 and a distal end 110. An actuator (i.e., a piston or plunger 120) may be slidably disposed within the chamber 106. Movement of the plunger 120 along a longitudinal axis 122 in either direction can affect the pressure within chamber 106. In some embodiments, the chamber 106 is integral to the device 100. In other embodiments, the chamber 106 is separately attachable to device 100.

In some examples, the injection device 100 includes a sensor 107 (e.g., a mechanical sensor or a capacitive sensor) for detecting a contact between the apparatus and the skin of a patient. In some examples, the sensor 107 is configured to detect an angle of the cartridge relative to the skin of the patient. In some examples, the sensor 107 is configured to detect a position of the injection opening relative to the patient's skin 115 or body. In some examples, the sensor 107 communicates with the injection controller 100 to prevent injection from occurring when the apparatus is not in contact with the patient's skin 115 or when an angle or position of the apparatus relative to the patient is incorrect.

1.1 Rotary Motor

The injection device 100 may include an electromagnetic rotary motor 126 that applies a force to the plunger 120 via a linkage 130 to inject the injectate in the chamber 106 through the skin 115. The linkage may include a ball screw actuator 130, and the linkage may also or instead include any other suitable mechanical coupling for transferring a rotary force of the rotary motor 126 into a linear force suitable for displacing injectate from the chamber 106. For example, the linkage may include one or more of lead screws, linear motion bearings, and worm drives, or another other suitable mechanical components or combination of mechanical components. As noted above, linear motion may usefully be inferred from rotation of a lead screw or the like, and the injection device 100 may be instrumented to monitor rotation in order to provide feedback on a position of the plunger 120 to a controller during an injection.

Figure 2:
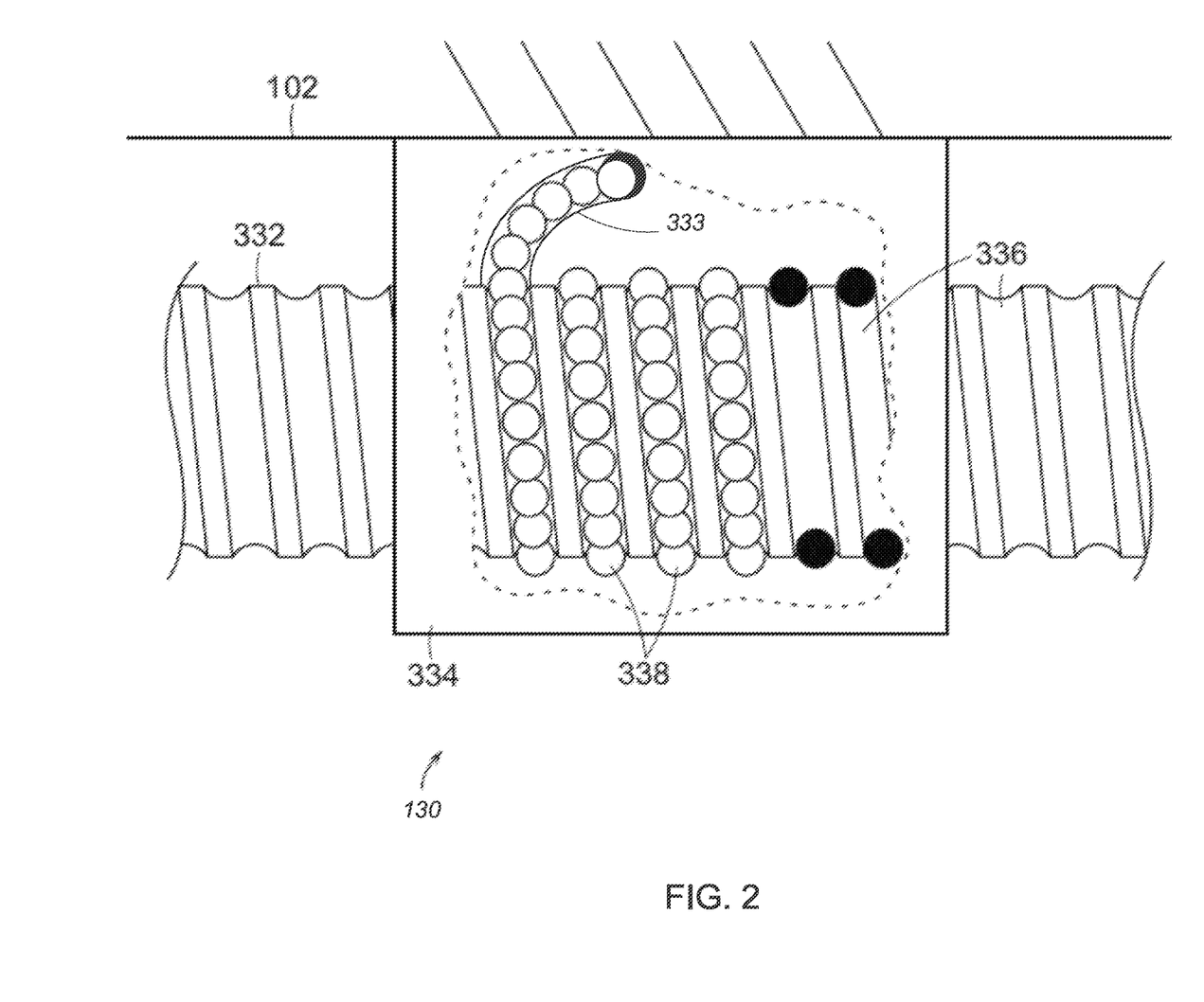
FIG. 2 is a cut-away diagram of a ball screw actuator.

Referring to FIG. 2, one example of a ball screw actuator 130 includes a screw 332 and a nut 334 (which is coupled to the housing 102 in FIG. 1), each with matching helical grooves 336. The ball screw actuator 130 may include a recirculating ball screw with a number of miniature balls 338 or similar bearings or the like that recirculate through the grooves 336 and provide rolling contact between the nut 334 and the screw 332. The nut 334 may include a return system 333 and a deflector (not shown) which, when the screw 332 or nut 334 rotates, deflects the miniature balls 338 into the return system. The balls 338 travel through the return system to the opposite end of the nut 334 in a continuous path. The balls 338 then exit from the ball return system into the grooves 336. In this way, the balls 338 continuously recirculate in a closed circuit as the screw 332 moves relative to the nut 334.

In some examples, the rotary motor 126 is of a type selected from a variety of rotational electrical motors (e.g., a brushless DC motor). The rotary motor 126 is configured to move the screw 332 of the ball screw actuator 130 back and forth along the longitudinal axis 122 by applying a torque (i.e., $\tau_M$) to either the screw 332 or the nut 334 of the ball screw actuator. The torque causes rotation of either the screw 332 or the nut 334, which in turn causes an input force $F_M(t)$, which is proportional to the torque applied by the motor, to be applied to the screw 332.

The torque $\tau_M$ applied to the screw 332 causes application of a force $F_P$ to the plunger 120 which in turn causes movement of the plunger 120 along the longitudinal axis 122. The force $F_P$ is determined according to the following equation representing an idealized relationship between torque and force for a ball screw actuator:

$$F_P = \frac{\tau_M 2\pi\eta}{P}$$

where $F_P$ is a force applied to the plunger 120 by the screw 332, $\tau_M$ is a torque applied to the screw 332, $\eta$ is an efficiency of the ball screw actuator 130, and P is a lead of the screw 332.

1.2 Control Loop

Referring again to FIG. 1, the transdermal injection device 100 may include a displacement sensor 140, an injection controller 135, and a three-phase motor controller 141. In general, the displacement sensor 140 measures a displacement x(t) of the screw 332 of the ball screw actuator 130 and/or the plunger 120. The displacement sensor 140 may, for example, measure an incremental displacement of the screw 332 by storing an initial displacement value (i.e., x(0)) and monitoring a deviation from the starting value over time. In other examples, the displacement sensor 140 measures an absolute displacement of the screw 332 relative to a position of the displacement sensor 140 or some other fixed reference point. In another aspect, the displacement sensor 140 may be coupled to a nut or other component of a ball screw that controls linear movement. In this configuration, the displacement sensor 140 can measure rotation of the screw drive, and rotational motion may be computationally converted into linear displacement for purposes of controlling operation of the device 100.

The displacement x(t) measured by (or calculated using data from) the displacement sensor 140 may be provided as input to the injection controller 135. As is described in greater detail below, the injection controller 135 processes the displacement x(t) to determine a motor control signal y(t). The motor control signal y(t) is provided to the three-phase motor controller 141 which, in conjunction with a power supply 143, drives the rotary motor 126 according to the motor control signal y(t). The motor 126 causes the torque $\tau_M(t)$ to be applied to the screw 332. The motor torque, $\tau_M(t)$ causes movement of the screw 332 (or any other suitable linear actuator) in a direction along the longitudinal axis 122.

1.3 System Diagram

Figure 3:
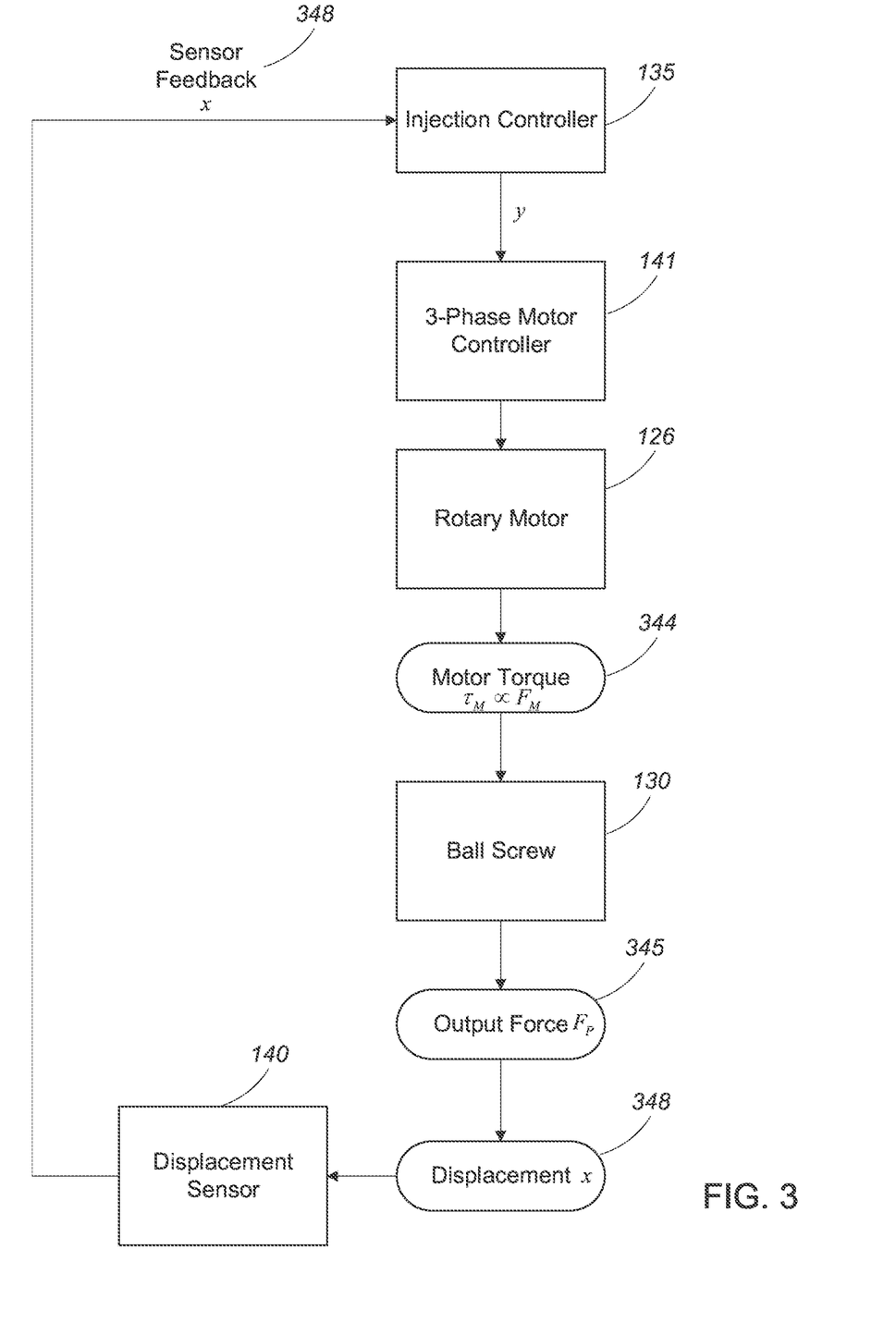
FIG. 3 is a block diagram of the controllable, needle-free transdermal injection device of FIG. 1.

Referring to FIG. 3, a schematic diagram of the system of FIG. 1 shows the rotary motor torque $\tau_M$ being applied to the ball screw 130 in step 344. Application of the rotary motor torque, at a given time $t_1$ by the rotary motor causes application of a force, $F_M(t_1)$ to the screw 332 of the ball screw 130 as shown in step 345, which in turn causes a displacement of the screw 332 in step 348.

The displacement of the screw 332 of the ball screw 130 is measured by the displacement sensor 140 and is fed back to the injection controller 135. As is described in greater detail below, the injection controller 135 processes the measured displacement to provide sensor feedback 348 to determine a motor control signal $y(t_1)$ which is supplied to the three-phase motor controller 141. The three-phase motor controller 141 drives the rotary motor 326 according to the motor control signal $y(t_1)$, causing the motor 126 to apply a torque $\tau_M(t_2)$ to the screw 332 of the ball screw 130 at a time $t_2$. As is noted above, the torque $\tau_M$ applied to the screw 332 causes application of a force $F_P$ to the plunger 120 with $F_P$ being determined as:

$$F_P = \frac{\tau_M 2\pi\eta}{P}$$

where $F_P$ is a force applied to the plunger 120 by the screw 332, $\tau_M$ is a torque applied to the screw 332, $\eta$ is an efficiency of the ball screw actuator 130, and P is a lead of the screw 332.

Figure 4:
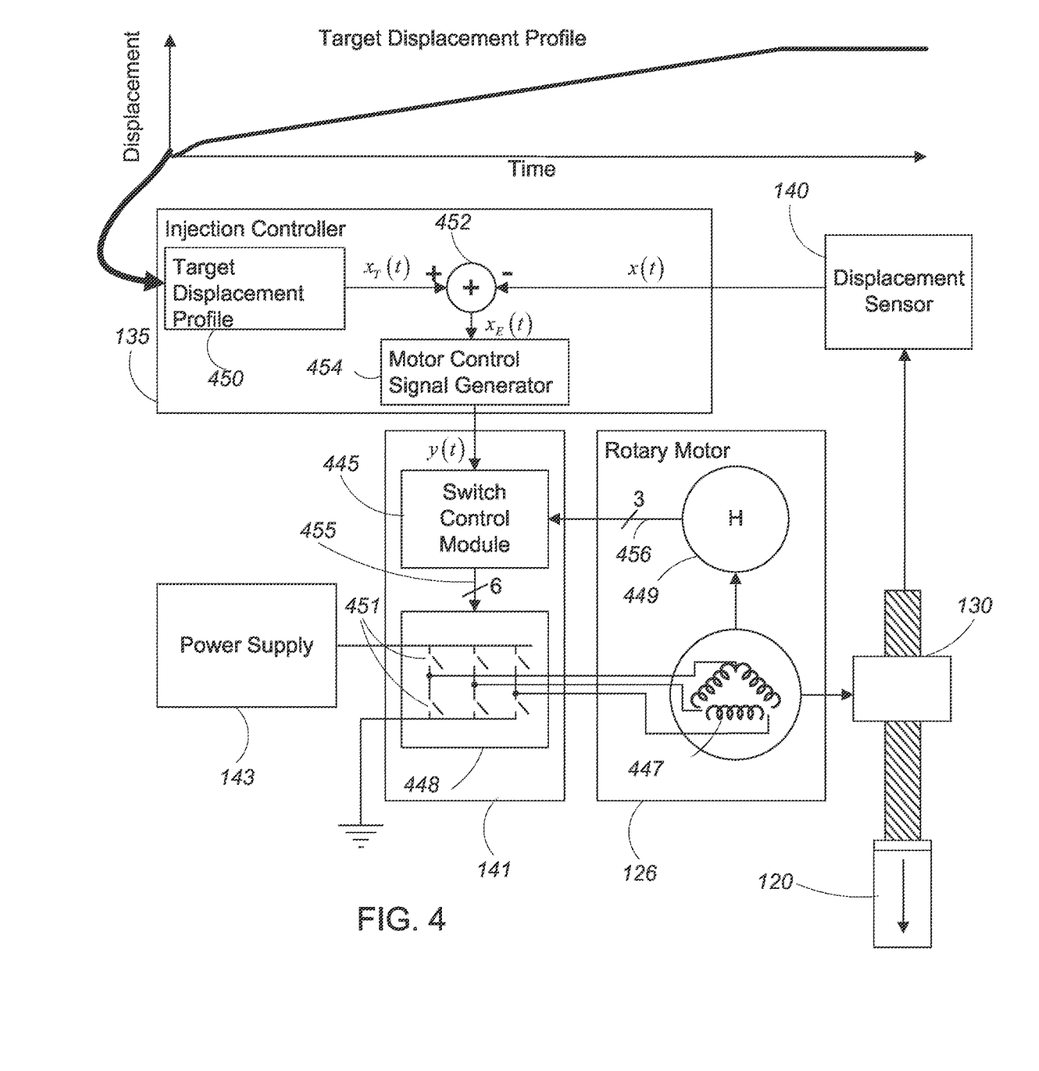
FIG. 4 is a detailed block diagram of the controllable, needle-free transdermal injection device of FIG. 1.

Referring to FIG. 4, in some examples the injection controller 135 includes a target displacement profile 450, a summing block 452, and a motor control signal generator 454. Very generally, the injection controller 135 receives a displacement value x(t) at time t from the displacement sensor 140. The time t is provided to the target displacement profile 450, which determines a target displacement value $x_T(t)$ for the time t.

In some examples, the target displacement profile 450 includes a mapping between target displacement values and times associated with an injection cycle (i.e., a range of time over which the plunger 120 of the device moves). For example, in the target displacement profile 450 shown in FIG. 4 the displacement starts at zero at the beginning of an injection cycle (i.e., at time $t_0$) and changes (e.g., increases) over time as the injection cycle proceeds, with each instant in time of the injection cycle being associated with a corresponding displacement value. As is described in greater detail below, in some examples the rate of change of the displacement values varies over time, with different time intervals of the injection cycle being associated with different rates of change of displacement values. Control of the plunger displacement, e.g., according to the target displacement profile 450, can be used to perform complex injections. For example, in one aspect, the plunger 120 is displaced relatively quickly during an initial piercing phase to penetrate the skin barrier, and in other time intervals the plunger 120 is displaced relatively slowly to deliver the injectate through an opening formed during the initial, piercing phase. In another aspect, the target displacement profile 450 may control multiple, sequential injections each having a biphasic profile with a piercing phase and a drug delivery phase. In practice, the actual displacement profile of the plunger 120 may vary from the ideal target displacement profile according to physical limits of the system and other constraints.

Both the measured displacement value x(t) and the target displacement value $x_T(t)$ are provided to the summing block 452. The summing block 452 subtracts the measured displacement value x(t) from the target displacement value $x_T(t)$ to obtain an error signal $x_E(t)$. The error signal $x_E(t)$ is provided to the motor control signal generator 454 which converts the error signal to a motor control signal y(t). The motor control signal y(t) is provided to the three-phase motor controller 141 or other suitable drive system, which in turn drives the motor 126 according to the motor control signal y(t).

In some examples, the rotary motor 126 may be a three-phase motor with three windings 447 and three Hall sensors 449, each Hall sensor 449 corresponding to a different one of the three windings 447. Each of the windings 447 is wrapped around a laminated soft iron magnetic core (not shown) so as to form magnetic poles when energized with current. Each of the three Hall sensors 449 generates a corresponding output signal 456 in response to presence (or lack of) a magnetic field in its corresponding winding 447.

The three-phase motor controller 141 includes a switch control module 445 and a switching module 448. The switching module 448 includes three pairs of switches 451 (with six switches 451 in total), each pair of switches corresponding to a different one of the windings 447 of the rotary motor 126 and configurable to place the corresponding winding 447 into electrical connection with the power supply 143 (whereby the winding is energized) or with ground. The switch control module 445 receives the motor control signal y(t) from the injection controller 135 and the three Hall sensor output signals 456 as inputs and processes the inputs to generate six switch control signals 455, each switch control signal 455 configured to either open or close a corresponding switch 451 of the switching module 448.

The above-described configuration implements a feedback control approach to ensure that a combination of the controlled torque applied to the screw 332 of the ball screw 130 due to the motor 126 causes the displacement of the plunger to track the target displacement profile 450 as the screw 332 is displaced.

1.4 Power Supply

Figure 5:
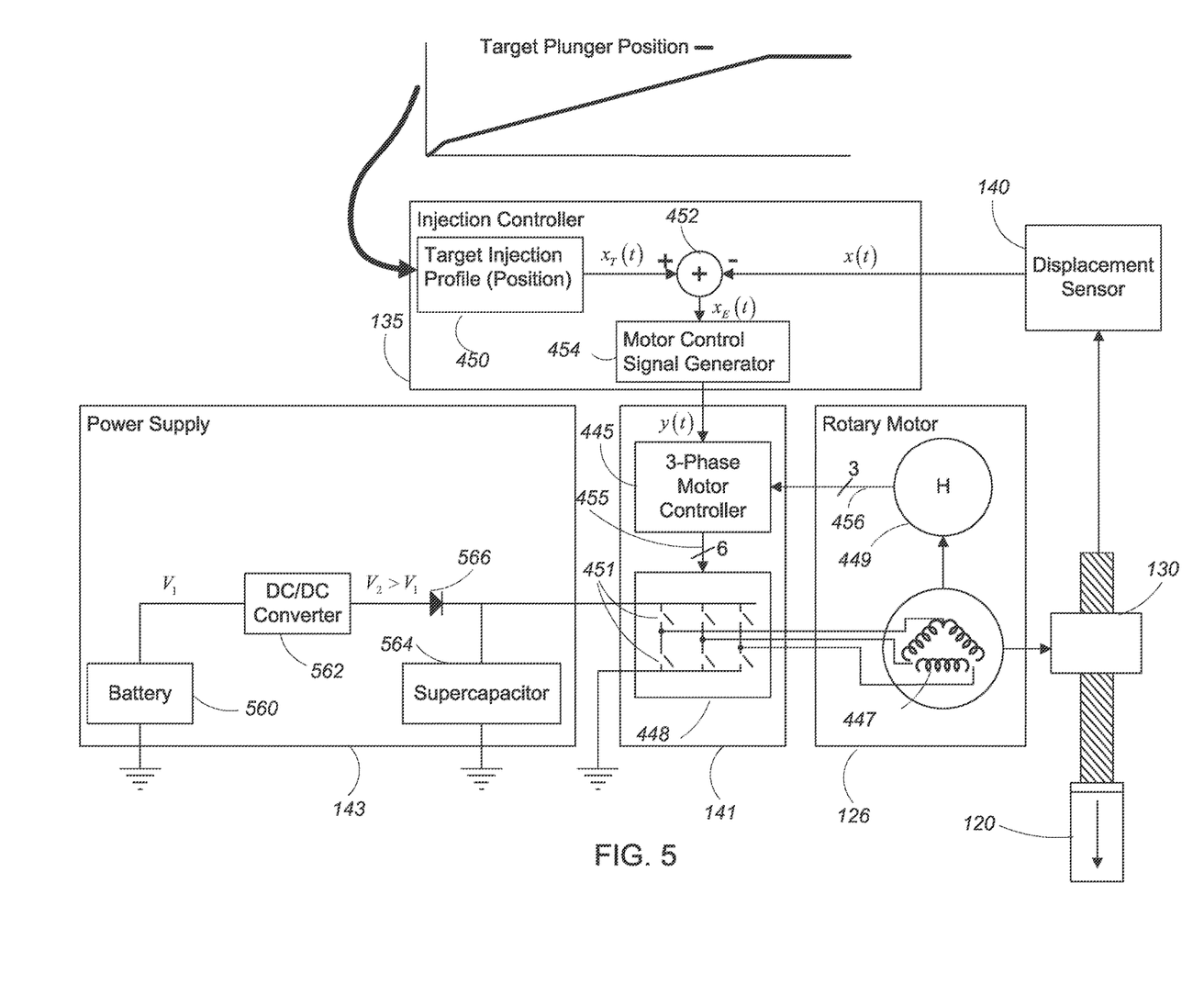
FIG. 5 is a detailed block diagram of the power supply of the controllable, needle-free transdermal injection device of FIG. 1.

Referring to FIG. 5, in some examples, the power supply includes a battery 560 (e.g., a Nickel Cadmium battery, a Nickel-Metal Hydride battery, a Lithium ion battery, an alkaline battery, or any other suitable battery type) configured to supply a voltage $V_1$ to a DC/DC converter 562 (e.g., a boost converter). The DC/DC converter 562 receives the supply voltage $V_1$ from the battery 560 as input and generates an output voltage $V_2$ greater than $V_1$. In some examples, the DC/DC converter 562 is configured to boost the supply voltage by a factor in the range of 5 to 20. While the battery 560 may be rechargeable, the battery 560 may also usefully store sufficient energy for multiple injections, such as two or more one milliliter injections, e.g., from replaceable single-dose cartridges or from a single, multi-dose cartridge.

The output voltage $V_2$ may be provided in parallel to a supercapacitor 564 and to the switching module 448 of the three-phase motor controller 141 via a diode 566. In operation, the output voltage $V_2$ charges the supercapacitor 564 while the transdermal injection device 100 is inactive. When an injection operation commences, the switches 451 of the switching module 448 close (according to the switch control signals 455), connecting the windings 447 of the rotary motor 126 to the supercapacitor 564. This results in a discharge of the supercapacitor 564, causing current to flow through the windings 447 of the rotary motor 126 and induce rotation of the rotary motor 126.

In some examples, the supercapacitor 564 includes a number of supercapacitors coupled together with a switching network. When the transdermal injection device 100 is inactive, the switching network may be configured so that the number of supercapacitors is connected in parallel for charging. When an injection is initiated, the switching network may be reconfigured so that the number of supercapacitors are serially connected for discharge. In some examples, the supercapacitor 564 is configured to deliver a peak power of 200 Watts or more to the ball screw 130 via the rotary motor 126.

In general, the supercapacitor may be any high-capacity capacitor suitable for accepting and delivering charge more quickly than a battery or other source of electrical energy. A wide variety of supercapacitor designs are known in the art and may be adapted for use as the supercapacitor 564 contemplated herein, such as double-layer capacitors, pseudocapacitors, and hybrid capacitors. Similarly, the supercapacitor 564 may usefully include any number and arrangement of supercapacitors suitable for delivering electrical power in an amount and at a rate suitable for driving a rotary motor 126 of an injection device 100 as contemplated herein.

2 Target Displacement Profile

Figure 6:
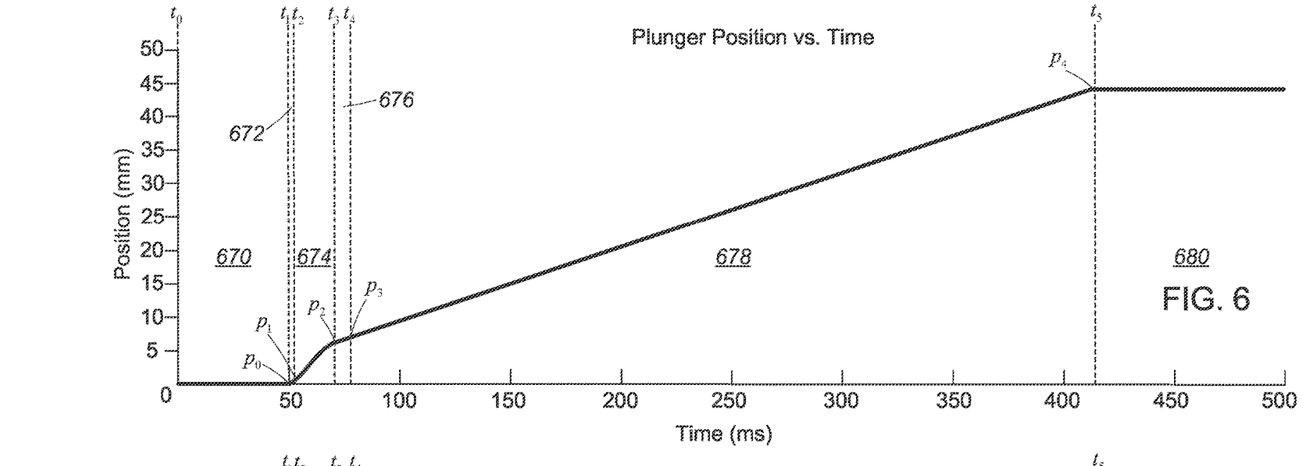
FIG. 6 is a target displacement profile.

Referring to FIG. 6, one example of a target displacement profile includes a number of injection phases, each associated with a corresponding time interval.

A first injection phase 670 is associated with a first time interval extending from time $t_0$ to time $t_1$. In the first injection phase 670, the target displacement of the plunger 120 is at a constant initial position $p_0$ where the plunger 120 is engaged with the injectate in the chamber 106. In this phase, the injection device 100 is generally prepared to perform an injection operation. In general, the first injection phase 670 may be preceded by any number of preparatory steps or phases, such as loading of an injectate (or a cartridge containing an injected) into the injection device, the removal of bubbles from the injectate as necessary or appropriate, measuring environmental conditions, measuring parameters of an injection site, and any other steps or combination of steps useful for performing, or preparing to perform, a needle-free injection as contemplated herein.

In one aspect, the rotary motor 126 may be mechanically engaged with the ball screw actuator 130 (or any other suitable linear actuator) while the rotary motor 126 is stationary in the first injection phase 670. That is, the rotary motor 126 may be pre-engaged with the ball screw actuator 130 and preload to remove any mechanical slack in the mechanical components of the system. In this configuration, a mechanical switch or the like may be used to prevent relative movement of the components, and/or a gate or seal may be used at the nozzle exit to prevent leakage of drug from the chamber 106. In another aspect, the rotary motor 126 may be slightly spaced apart from engagement with the ball screw actuator 130. In this latter configuration, the rotary motor 126 may usefully accelerate (while unloaded) into engagement with the ball screw actuator 130 at an end of the first injection phase 670 or at a beginning of the second injection phase 672 to facilitate a greater initial velocity of injectate from the nozzle. This may, for example, include a single rotation of the rotary motor 126 from engagement with the ball screw actuator 130, or a fractional rotation suitable to facilitate very high initial rotational acceleration.

A second injection phase 672 is associated with a second time interval extending from time $t_1$ to $t_2$. In the second injection phase 672, movement of the plunger 120 may be initiated. In this phase, the target displacement of the plunger 120 increases at a relatively high first rate to move the plunger 120 from the initial position $p_0$ to a first position $p_1$. In general, the motion of the plunger 120 in this phase may cause a jet of injectate to be ejected from the chamber 106 of the injector head 104 (via the opening 114) with a first velocity $V_1$ at least sufficient to pierce human tissue to a subcutaneous depth. In some examples, the second injection phase 672 spans a time interval less than 100 ms (i.e., the difference between $t_1$ and $t_2$ is less than 100 ms). In some examples, the second injection phase 672 spans a time interval less than 60 ms (i.e., the difference between $t_1$ and $t_2$ is less than 60 ms). In some examples, the second injection phase 672 spans a time interval less than 10 ms (i.e., the difference between $t_1$ and $t_2$ is less than 10 ms).

More generally, the injection device 100 may be configured so that in this second injection phase 672, the plunger 120 transitions from a stationary position to the target velocity at a sufficient rate for the initial stream of injectate to achieve a piercing velocity substantially instantaneously, e.g., without substantial leakage or loss of injectate at the surface. By configuring the linear drive system described above to accelerate in this manner from a fixed position to a piercing velocity, the injection device 100 may advantageously mitigate loss of injectate. As a further advantage, an injection device with this capability can usefully perform multiple sequential injections without requiring any physical recharge or resetting of a mechanical stored energy system.

A third injection phase 674 is associated with a third time interval extending from time $t_2$ to $t_3$. In the third injection phase 674 the target displacement of the plunger 120 increases at a rate substantially the same as the first rate to move the plunger 120 from the first position $p_1$ to the second position $p_2$. In this third injection phase 674, the plunger 120 may be moved at a rate to cause the jet of injectate to be ejected from the chamber 106 of the injector head 104 with a second velocity $V_2$ greater than or equal to the first velocity $V_1$. While the rate of plunger 120 movement and the velocity of the injectate stream may vary within this third injection phase 674, e.g., according to limitations on control precision, physical system components, and so forth, the plunger 120 should generally be driven at a minimum velocity suitable for piercing tissue at a target site to a desired depth for delivery of the injectate. The jet of injectate may also have a maximum velocity selected to avoid over-penetration or other undesirable tissue damage.

A fourth injection phase 676 is associated with a fourth time interval extending from time $t_3$ to time $t_4$. In the fourth injection phase 676 the target displacement of the plunger 120 increases at a third rate, relatively slower than the first rate, to move the plunger 120 from the second position $p_2$ to a third position $p_3$. In this fourth injection 676, the injection device 100 may generally decelerate the plunger 120 to cause the jet of injectate to eject from the chamber 106 of the injector head 104 with a third velocity $V_3$ less than the first velocity $V_1$, which may generally be any velocity suitable for non-piercing delivery of additional injectate at a current depth of the stream of injectate within the target tissue.

A fifth injection phase 678 is associated with a fifth time interval extending from time $t_4$ to $t_5$. In the fifth injection phase 678 the target displacement of the plunger 120 continues to increase at the third rate to move the plunger 120 from the third position $p_3$ to the fourth position $p_4$. In the fifth injection phase 678, the injection device 100 may generally deliver the injectate—typically a majority of the injectate in the chamber 106—at a subcutaneous depth achieved during the prior, piercing phase. The rate of movement may be generally constant, or may otherwise vary consistent with maintaining subcutaneous drug delivery without further piercing of the tissue.

It will be appreciated that some continued piercing may occur during the fifth injection phase 678. Provided that any additional piercing does not create a pathway below subcutaneous depth within the target tissue that might result in loss or misdelivery of therapeutic dosage, then this additional piercing will not affect the efficacy of transdermal drug delivery. It will also be understood that the total displacement of the plunger 120 will control the volume of drug delivered over the course of an injection, and a duration of the fifth injection phase 678 may correspondingly be selected according to an intended dosage.

Finally, a sixth injection phase 680 occurs after time $t_5$. In the sixth injection phase 680 the target displacement of the plunger 120 stops increasing, substantially halting the plunger 120 at a fourth position $p_4$. The sixth injection phase 680 is associated with completion of the injection operation. As noted above, from this position, additional injection cycles may be initiated, provided of course that sufficient additional drug remains in the injection device 100 for completing additional injections.

In order to quickly achieve a piercing velocity and avoid loss of drug at the surface of an injection site, the second injection phase 672 (where acceleration of the injectate occurs) may be short relative to the piercing phase that is maintained once the piercing velocity is achieved. Thus in some examples, the time interval associated with the third injection phase 674 is in a range of two to twenty times as long as the time interval associated with the second injection phase 672. In some examples, the time interval associated with the second injection phase 672 has a duration between 30 milliseconds and 100 milliseconds and the time interval associated with the third injection phase 674 has a duration between 100 milliseconds and 1000 milliseconds.

More generally, the duration of each phase may depend on the diameter of the injectate stream, the properties of the injectate, the characteristics of the tissue at the injection site and so forth. Thus, the injection profile may usefully employ any durations suitable for accelerating to a piercing velocity sufficiently rapidly to avoid substantial loss of injectate, maintaining a piercing velocity until a target depth (e.g., subcutaneous depth) is achieved, and then maintaining a non-piercing velocity to deliver a full dose at the target depth.

It will also be understood that, while a single injection cycle is illustrated, the injection device 100 contemplated herein may usefully be configured for multiple, sequential injections. As such any number of injection cycles might usefully be performed, and any such multi-injection applications are expressly contemplated by this description.

2.1 Rotary Motor Speed

Figure 7:
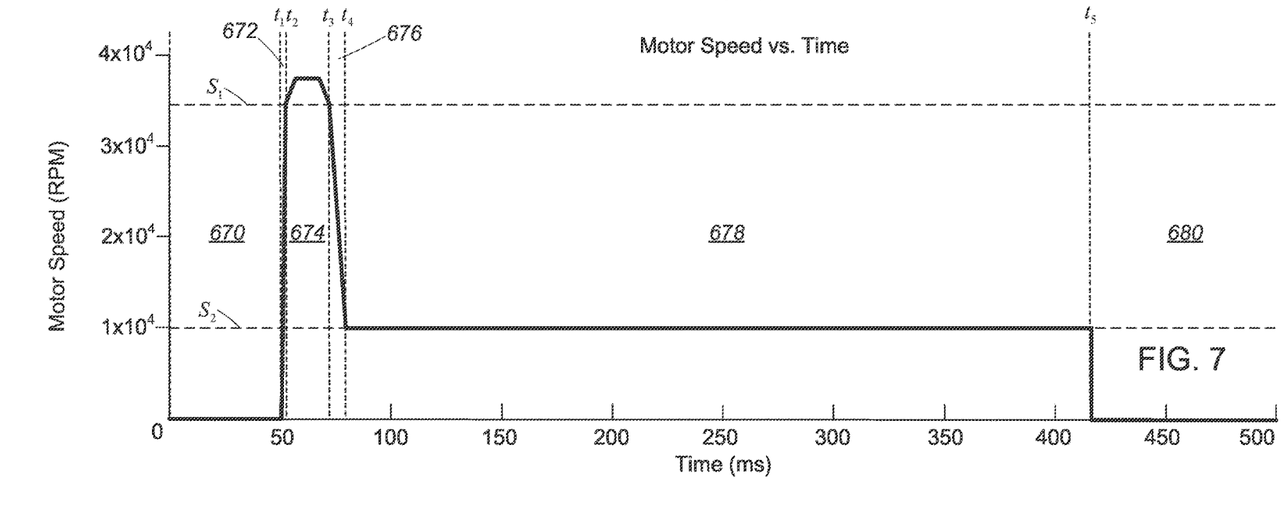
FIG. 7 is a rotary motor speed profile associated with the target displacement profile of FIG. 6.

Referring to FIG. 7, in the first injection phase 670, the injection controller 135 controls the rotary motor 126 to maintain its speed at substantially 0 rotations per minute (RPM) to ensure that the plunger 120 remains stationary at the initial position $p_0$. This may include actively maintaining the rotary motor 126 in a fixed position, e.g., by monitoring the position and activation the rotary motor 126 in counter-response to any detected motion or drift, or by control a magnetic, mechanical, or electromechanical lock that securely engages the plunger 120 in the initial position $p_0$. In another aspect, this may include passively maintaining the rotary motor 126 in the fixed position by withholding control signals or drive signals from the rotary motor 126. It will also be understood that combinations of the foregoing may advantageously be employed. For example, the plunger 120 may be locked with a mechanical lock during storage or while otherwise not in use, and then the rotary motor 126 may be used to electromechanically and actively lock the position of the plunger 120 when the mechanical lock is disengaged to prepare for an injection. In this manner, power may be conserved during long term storage, while the position can be securely and controllably locked using the rotary motor 126 in an interval immediately prior to injection in order to prevent, e.g., leakage of an injectate.

In the second injection phase 672, the injection controller 135 may control the rotary motor to accelerate from 0 RPM to a first rotary motor speed $S_1$ (e.g., 33,000 RPM), causing the plunger 120 to move from the initial position $p_0$ to the first position $p_1$. In the third injection phase 674, the injection controller 135 may control the rotary motor 126 to maintain a speed at or above the first rotary motor speed $S_1$, causing the plunger 120 to move from the first position $p_1$ to the second position $p_2$. In the fourth injection phase 676, the injection controller 135 may control the rotary motor 126 to decelerate to a second rotary motor speed $S_2$ (e.g., 11,000 RPM) less than the first rotary motor speed $S_1$, causing the plunger 120 to move from the second position $p_2$ to a third position $p_3$. In the fifth injection phase 678, the injection controller 135 may control the rotary motor 126 to maintain the second rotary motor speed $S_2$, causing the plunger 120 to move from the third position $p_3$ to a fourth position $p_4$ at a substantially consistent rate for delivery of an injectate at a target depth for an injection.

In the sixth injection phase, the injection controller 135 may control the rotary motor 126 to decelerate its speed from the second rotary motor speed $S_2$ to 0 RPM, causing movement of the plunger 120 to substantially halt at the fourth position $p_4$.

While the supercapacitor 564 in the power supply 143 described above may be used during any portion of the injection delivery, the supercapacitor 564 may be particularly advantageous where high mechanical loads are anticipated, e.g., during the initial acceleration and piercing phases, as well as where necessary or helpful to quickly decelerate or stop the plunger 120, e.g., at the fourth position $p_4$. Thus, the supercapacitor 564 may be specifically used during the second injection phase 672, the third injection phase 674, and optionally the fourth injection phase 676 if high power is required to maintain a target speed even during a deceleration of the injectate to a drug delivery velocity, and/or if high power is required to quickly decelerate or stop the plunger 120.

2.2 Injectate Velocity

Figure 8:
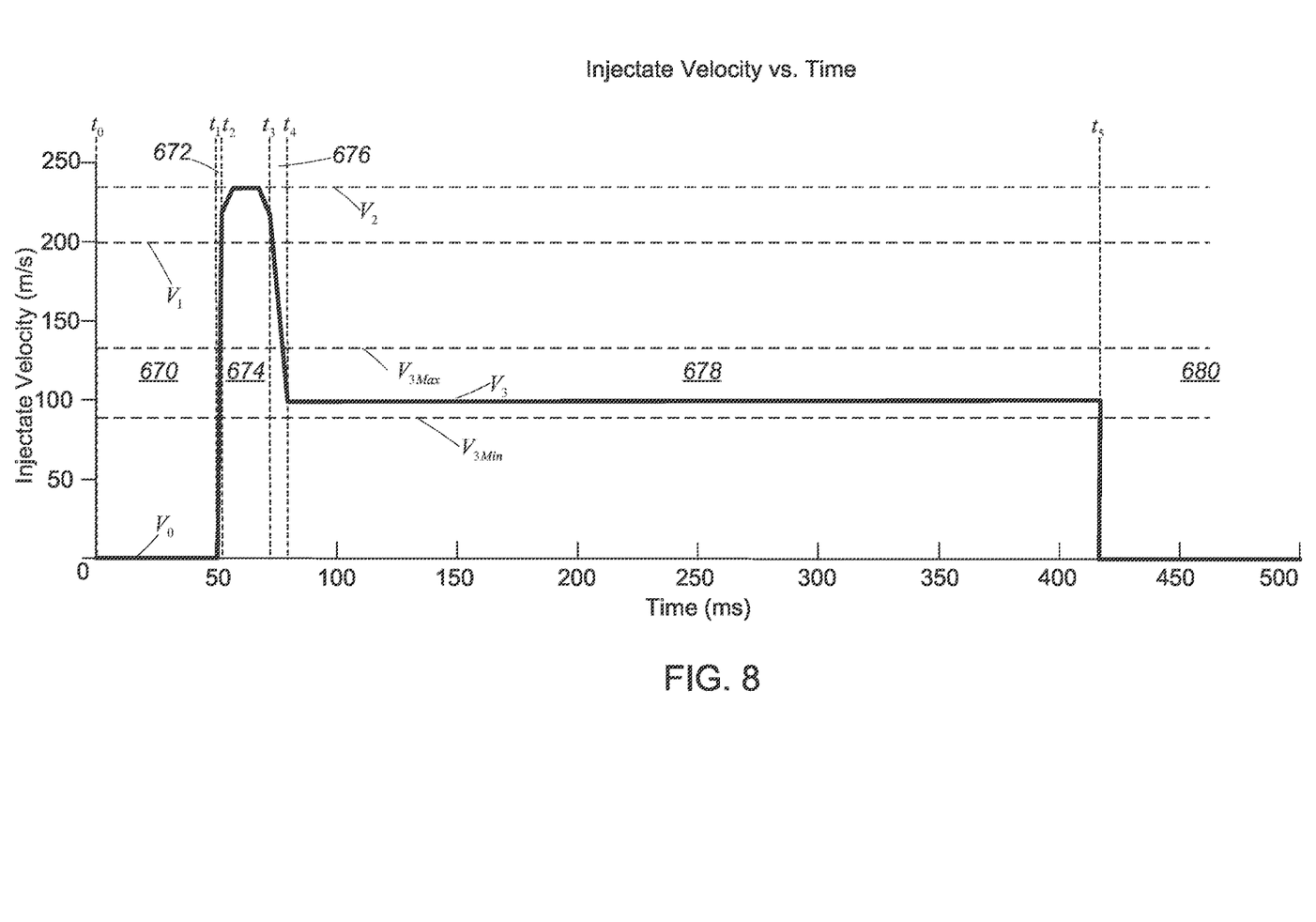
FIG. 8 is an injectate jet velocity profile associated with the target displacement profile of FIG. 6.

Referring to FIG. 8, in the first injection phase 670, no injectate is ejected from the chamber 106 (i.e., the initial injectate velocity, $V_0$ is 0 m/s). In the second injection phase 672, the injectate velocity increases from 0 m/s to the first velocity, $V_1$ at least sufficient to pierce human tissue. In some examples, the first velocity $V_1$ is at least 200 m/s. If piercing is not initiated quickly, then there may be substantial loss or leakage of drug. Thus, in some embodiments, the rotary motor 126 may usefully be configured to reach the first velocity $V_1$ for injection from a stationary starting point in not more than three rotations, such as less than two rotations, or less than one rotation.

In the third injection phase 674, the injectate velocity may be maintained at a second velocity $V_2$ greater than or equal to the first velocity $V_1$ in order to continue piercing tissue at a target site. Where the first velocity $V_1$ is a minimum velocity for piercing tissue, then the second velocity $V_2$ is preferably maintained above the first velocity $V_1$ in order to continue piercing throughout the third injection phase 674. However, the first velocity $V_1$ may instead be a minimum velocity or an optimum velocity to initiate piercing, in which case the second velocity $V_2$ may usefully be any velocity greater than, equal to, or less than the first velocity $V_1$ suitable for continuing to pierce tissue to the desired, target depth. Similarly, the second velocity $V_2$ may vary over the duration of the third injection phase 674 provided that the second velocity $V_2$ remains within this window of useful piercing velocities.

In the fourth injection phase 676, the injectate velocity may decreases to a third velocity $V_3$ (in a range between a maximum third velocity $V_{3Max}$ and a minimum third velocity $V_{3Min}$) sufficient to deliver the majority of the injectate in the chamber 106 at a subcutaneous depth. In the fifth injection phase 678, the injectate velocity may be substantially maintained at the third velocity $V_3$ while the majority of the injectate in the chamber 106 is delivered to the subcutaneous depth through the channel created during the third injection phase 674. It will be appreciated that the third velocity $V_3$ may vary over the course of the fifth injection phase 678 between any values—typically greater than zero and less than a piercing velocity—consistent with delivery of the injectate at the target depth. Finally, in the sixth injection phase 680, the injectate velocity may decrease to 0 m/s as the injection operation completes.

3 Injectate

In some examples, the volume of injectate in the chamber is at least one milliliter. Thus, in one aspect the injection device 100 may be configured to deliver one milliliter of drug subcutaneously in a single dose, or as a number of sequential doses over time, e.g., to different locations or over the course of an extended dosing schedule. Where a large number of sequential doses are intended, or where a larger single dose is intended (e.g., more than one milliliter) the chamber may usefully have a greater volume. For multi-dose applications, the contents of the chamber 106 may be conveniently distributed in discrete doses using a rotary motor and linear drive system as contemplated herein. In some examples, the volume of injectate in the chamber is less than or equal to approximately 0.5 milliliters. In some examples, the volume of injectate in the chamber is less than or equal to approximately 0.3 milliliters. In some examples, the volume of injectate in the chamber is a therapeutic amount of injectate.

In some examples, the injectate includes a biological drug. In some examples, the injectate has a viscosity of at least three centipoise at a temperature between two degrees and twenty degrees Celsius. In some examples, the injectate has a viscosity of about three centipoise to about two hundred centipoise at a temperature between two degrees and twenty degrees Celsius. Thus, the system described herein may usefully be employed with large molecule therapeutics or other drugs having relatively high viscosities.

4 Miscellaneous

In one aspect, the injection controller may be configured to cause the needle-free transdermal injection device 100 to perform a number of sequential injection operations in close temporal proximity to one another. The injection device 100 may usefully be instrumented to support this operation by sensing movement of the injection device 100 and providing tactile, visible, audible or other feedback to aid in navigating the user through a multi-injection procedure.

In another aspect, a number of sequential injection operations may be performed without having to reverse the movement of the rotary motor (i.e., to withdraw the plunger). Thus, where additional injectate remains in the injection device 100 at the end of an injection cycle sufficient for an additional dose, the rotary motor 126 may remain stationary, and a second, complete injection cycle may be initiated from this new starting position. In this context, the rotary motor 126 may be manually locked, or electromagnetically maintained in a fixed location in order to prevent leakage or other loss of therapeutic product.

In some examples, the linkage (e.g., the ball screw linkage) is bidirectionally coupled to the rotary motor and the plunger such that bidirectional displacement of contents in the chamber is possible, e.g. by moving the plunger toward an exit nozzle to eject contents, or moving the plunger away from the exit nozzle to load additional drug into the injection device 100.

In some examples, the transdermal injection device includes a sensor system for detecting when the device is properly positioned for performing an injection operation. In some examples, once the device is properly positioned, the injection controller is configured to initiate the injection operation without any observable latency. That is, the sensor system may monitor the injection device 100, determine when the injection device 100 is properly positioned and stationary, and then initiate an injection. Depending on the duration and feel of the injection, the injection may usefully be preceded by a beep, vibration, or other human-perceptible signal alerting a user that the injection is about to occur.

In some examples, one or more conventional capacitors (e.g., electrolytic capacitors) can be used instead of the supercapacitor.

In some examples the injection controller is configured to prevent two or more injection operations within a predetermined minimum injection cycle time. Thus, for example, where a dosing regimen specifies a minimum time before injections, or where an injection is being delivered as a sequence of injections in different but adjacent locations, the injection controller may monitor activation of the injection device 100 to ensure that any rules for a corresponding injection protocol are adhered to.

In some examples, the needle-free transdermal injector head is formed as a removable cartridge for containing injectate. The removable cartridge has an opening with a predetermined shape for ejecting the injectate in a stream with a predetermined shape. In some examples, the needle-free transdermal injector includes a movable cartridge door mechanism. A user can interact with the movable cartridge door mechanism to load cartridges into the needle-free transdermal injector and to unload cartridges from the needle-free transdermal injector.

While the above description relates primarily to methods and apparatuses for the injection of therapeutics through human tissue to a subcutaneous depth, it is noted that, in some examples the methods and apparatuses described above are used for injection of therapeutics through human tissue to other shallower or deeper depths. For example, the methods and apparatuses can be used for a shallow injection of therapeutics into the dermis, or for a deeper injection though the subcutaneous layer of fat and connective tissue into a patient's musculature.

It is to be understood that the foregoing description is intended to illustrate and not to limit the scope of the invention, which is defined by the scope of the appended claims. Other embodiments are within the scope of the following claims.

What is claimed is:

1. An apparatus for injectate delivery comprising:
   a cartridge containing a volume of an injectate and an exit port;
   a linear actuator configured for delivery of the injectate from the exit port of the cartridge, the linear actuator including a linkage;
   a rotary motor mechanically coupled to the linkage;

a controller coupled to the rotary motor, wherein the controller is configured to control a linear motion of the linear actuator in response to a control signal by controlling an electrical input supplied to the rotary motor in:
- a first interval during which the rotary motor is engaged with the cartridge to displace the injectate therefrom,
- a second interval during which the controller drives the rotary motor to maintain a jet of the injectate at or above a first speed selected to create a channel through a human tissue to a subcutaneous depth, and
- a third interval during which the controller drives the rotary motor at a second speed less than the first speed and maintained within a range selected to deliver the volume of the injectate at the subcutaneous depth; and a sensor system configured to detect when the apparatus is properly positioned to deliver the injectate to a patient, wherein the controller is configured to prevent injection when a position of the apparatus relative to the patient is incorrect, and wherein the rotary motor provides sufficient power for the jet of the injectate to reach the first speed in not more than three rotations of the rotary motor.

2. The apparatus of claim 1 wherein the sensor system detects a contact of the apparatus with a skin of the patient.

3. The apparatus of claim 1 wherein the sensor system detects a second position of the exit port relative to a body of the patient.

4. The apparatus of claim 1 further comprising one or more supercapacitive energy storage elements.

5. The apparatus of claim 4 further comprising a power supply and wherein the one or more supercapacitive energy storage elements includes a plurality of supercapacitive energy storage elements and the power supply is configured to switch the plurality of supercapacitive energy storage elements into a parallel configuration during a charging operation and to switch the plurality of supercapacitive energy storage elements into a serial configuration for an injection operation.

6. The apparatus of claim 1 further comprising a power supply and a capacitive energy storage element including a plurality of capacitors.

7. The apparatus of claim 6 wherein the power supply is configured to switch the plurality of capacitors into a parallel configuration with a battery during a charging operation and to switch the plurality of capacitors into a serial configuration for an injection operation.

8. The apparatus of claim 6 wherein the power supply includes a battery and a direct current to direct current (DC/DC) converter disposed between the battery and the capacitive energy storage element.

9. The apparatus of claim 8 wherein the direct current to direct current (DC/DC) converter is configured to boost a voltage supplied by the battery by a factor in a range of 5-20.

10. The apparatus of claim 6 wherein the power supply includes a direct current to direct current (DC/DC) converter disposed between the capacitive energy storage element and the rotary motor.

11. The apparatus of claim 6 wherein substantially all of an electrical power supplied to the rotary motor during the second interval and the third interval is supplied from the capacitive energy storage element.

12. The apparatus of claim 1 wherein the controller is configured to prevent multiple injectate delivery operations within a predetermined minimum injection cycle time.

13. The apparatus of claim 1 wherein the third interval is in a range of two to twenty times as long as the second interval.

14. The apparatus of claim 1 wherein the second interval has a first duration of between 30 milliseconds and 100 milliseconds and the third interval has a second duration of between 100 milliseconds and 1000 milliseconds.

15. The apparatus of claim 1 wherein the cartridge is configured to be removably and replaceably coupled to the apparatus, and wherein the exit port has a predetermined shape for ejecting the injectate in a stream.

16. The apparatus of claim 1 wherein the sensor system detects an angle of the cartridge relative to a skin of the patient.

17. The apparatus of claim 1 wherein the controller and the rotary motor are configured to initiate delivery of the injectate when the apparatus is properly positioned.

18. The apparatus of claim 1 wherein the controller is configured to prevent injection until the apparatus is properly positioned.

19. The apparatus of claim 1 wherein the first speed and the second speed are less than a third speed applied between the first interval and the second interval and selected to create the jet of the injectate from the cartridge with a velocity at least sufficient to pierce the human tissue.

20. The apparatus of claim 1 wherein the injectate has a viscosity of between three centipoise and two hundred centipoise at a temperature between two degrees and twenty degrees Celsius.

* * * * *